United States Patent
Brown et al.

(10) Patent No.: US 8,273,694 B2
(45) Date of Patent: Sep. 25, 2012

(54) SYNTHETIC COMPOSITIONS OBTAINED FROM ALGAE

(75) Inventors: Jeffrey A. Brown, San Carlos, CA (US); Joseph A. Duimstra, San Carlos, CA (US); Jason R. Wells, San Francisco, CA (US)

(73) Assignee: Jeffrey A Brown, San Carlos, CA (US)

( * ) Notice: Subject to any disclaimer, the term of this patent is extended or adjusted under 35 U.S.C. 154(b) by 549 days.

(21) Appl. No.: 12/460,955

(22) Filed: Jul. 27, 2009

(65) Prior Publication Data

US 2010/0120643 A1    May 13, 2010

Related U.S. Application Data

(60) Provisional application No. 61/083,983, filed on Jul. 28, 2008.

(51) Int. Cl.
*C10M 105/36* (2006.01)
*C12P 7/64* (2006.01)
*C07C 67/02* (2006.01)

(52) U.S. Cl. ............ 508/496; 435/134; 560/263
(58) Field of Classification Search .......... 508/496; 435/134; 560/263
See application file for complete search history.

(56) References Cited

U.S. PATENT DOCUMENTS

2008/0242565 A1* 10/2008 Cherkasky ............ 508/112
2008/0248982 A1* 10/2008 Miller et al. ............ 508/485
2009/0285728 A1* 11/2009 Miller ............ 422/187

* cited by examiner

*Primary Examiner* — Cephia D Toomer
*Assistant Examiner* — Vishal Vasisth

(57) ABSTRACT

The application provides a base stock or a lubricant composition comprising the substances derived from algae by chemical modification of algal oil, including compositions comprising estomers. Methods for obtaining the same are also provided, including chemically modifying the algal oil with a saturated fatty acid under conditions favorable to the formation of a poly-estomer.

17 Claims, 3 Drawing Sheets

Process of Estomer Synthesis from Algal Oil

SYNTHETIC COMPOSITIONS OBTAINED FROM ALGAE

Figure 1 Process of Estomer Synthesis from Algal Oil

Figure 2 Process for Production of a Lubricant Formulation From Algae

SYNTHETIC COMPOSITIONS OBTAINED FROM ALGAE

CROSS-REFERENCE TO RELATED APPLICATIONS

This application is a non-provisional utility patent application claiming the priority and benefits of the following Provisional Patent Application, which is incorporated herein in it's entirety by reference:

1) Provisional Patent Application Ser. No. 61/083,983 filed on Jul. 28, 2008, entitled "SYNTHETIC COMPOSITIONS OBTAINED FROM ALGAE", which will be referred to as Reference 1.

TECHNICAL FIELD

This disclosure relates generally to the field of lubricants, and more specifically, to organic compositions obtained by chemical modification of algal oils for the use as base stocks in lubricant formulations.

BACKGROUND

Mineral oils from petroleum, natural oils from plants and animals, and synthetic esters such as polyol esters and poly-alphaolefins (PAOs) are commonly used as base stocks in the formulation of lubricants. Lubricants typically consist of 60-100% base stock by weight and the remainder in additives to control their fluid properties and improve low temperature behavior, oxidative stability, corrosion protection, demulsibility and water rejection, friction coefficients, lubricities, wear protection, air release, color and other properties. While the products traditionally used have many advantages and attractive properties, none of them is also free of drawbacks and disadvantages such as, for example, poor low temperature fluidity, and poor thermal oxidative stability, which leads to rapid degradation, thickening and deposit formation in use. An increasingly important characteristic for lubricants is environmental performance. The commonly used basestocks often suffer from the inability to bring together a high level of environmental performance such as biodegradability with traditional lubricant performance characteristics.

SUMMARY

We provide products useful for making base stocks and lubricants and methods for manufacturing thereof from algal oil, to capture many of the beneficial properties of natural oils while addressing their deficiencies to create an improved base oil for use in lubricant products.

We provide base stocks suitable for lubricant formulation, comprising a chemically modified algal oil, particularly the base stock, comprising a compound including a moiety having the chemical structure 1:

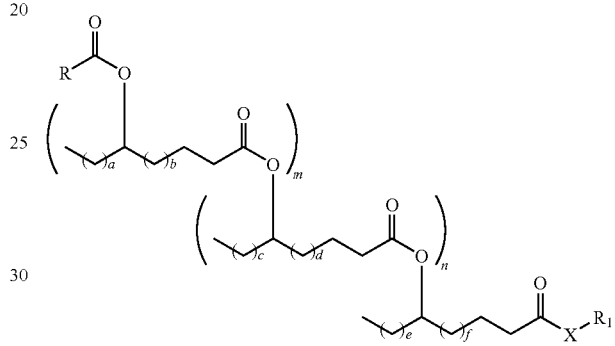

wherein R is a linear $C_1$-$C_{18}$ alkane; each of m and n is selected from the group consisting of 0 and a positive integer; each of the sums (a+b) and (c+d) is selected from the group consisting of 1, 3, 5, 7, 9, 11, 13, and 15; the sum (e+f) is selected from the group consisting of 9, 11, 13, and 15; X is selected from the group consisting of $NR_2$, O and S; and each of $R_1$ and $R_2$ is a $C_1$-$C_{30}$ hydrocarbon optionally containing linear, branched, saturated, unsaturated and/or aromatic functionalities.

We also provide base stocks, comprising a compound including a moiety having the chemical structure 2:

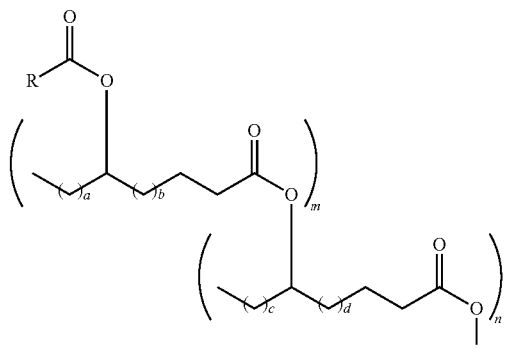

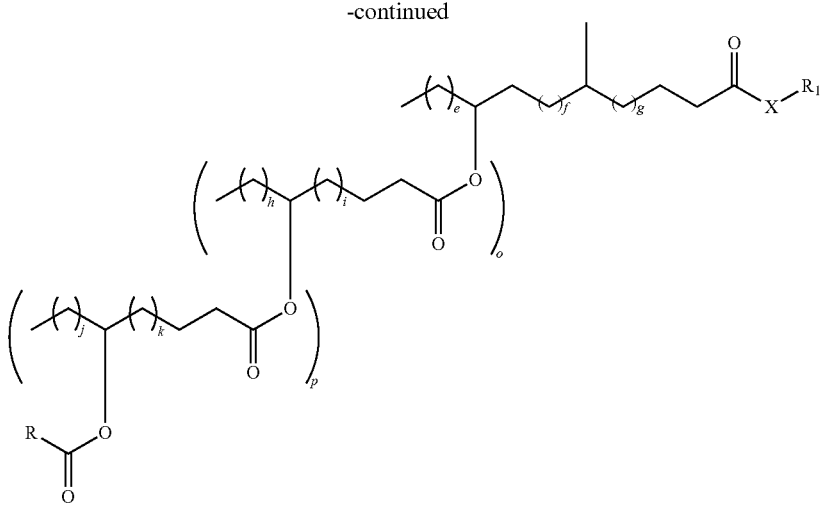

wherein R is a linear $C_1$-$C_{18}$ alkane; each of m, n, p, and o is selected from the group consisting of 0 and a positive integer; each of the sums (a+b), (c+d), (h+i) and (j+k) is selected from the group consisting of 1, 3, 5, 7, 9, 11, 13, and 15; the sum (e+f+g) is selected from the group consisting of 7, 9, 11, 13, and 15; X is selected from the group consisting of $NR_2$, O and S; and each of $R_1$ and $R_2$ is a $C_1$-$C_{30}$ hydrocarbon optionally containing linear, branched, saturated, unsaturated and/or aromatic functionalities.

We also provide methods for obtaining base stock derived from a chemically modified algal oil, including but not limited to base stock comprising compounds 1 and/or 2. The methods comprise cultivating and harvesting a species of algae, extracting algal oil from the harvested algae; and chemically modifying the extracted algal oil. The processes of chemical modification may include reacting the extracted algal oil with a saturated fatty acid under conditions favorable to the formation of a poly-estomer.

DETAILED DESCRIPTION

Figure 1:
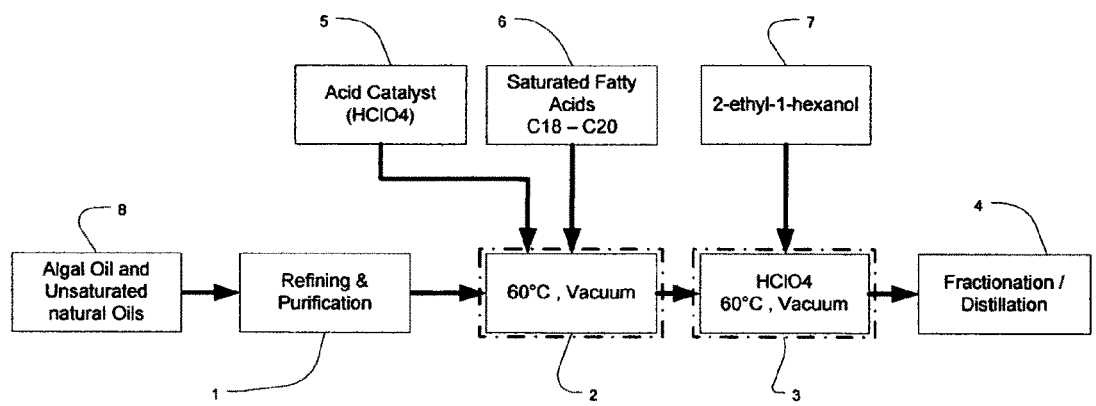
FIG. 1 is a block-diagram schematically illustrating a process of production of estomers from algal oil.

The following definitions are used below, unless otherwise described:

The term "algae" refers to a family of aquatic, eucaryotic single cell or multicellular plants without stems, roots and leaves, that are typically autotrophic, photosynthetic, contain chlorophyll, and grow in bodies of water, including fresh water, sea water, and brackish water, with the degree of growth being in relative proportion to the amount of nutrients available.

The term "microalgae" refers to photosynthetic protists that include a variety of unicellular, coenocytic, colonial, and multicellular organisms, such as the protozoans, slime molds, brown and red algae, algal strains, diatoms, cyanobacteria or the like. Microalgae contain lipids and fatty acids as membrane components, storage products, metabolites and sources of energy.

The term "algal oil" refers to, low polarity, predominantly hydrocarbon oil derived from algae.

The term "alkyl" refers to substituted and unsubstituted straight chain or branched saturated aliphatic hydrocarbon groups, such as methyl, ethyl, propyl, butyl, pentyl, hexyl, heptyl, octyl, nonyl, decyl, isopropyl, isobutyl, tert-butyl, sec-butyl, and the like.

The term "an olefin," also known as "alkene" or "alkylene" is defined as compounds containing at least one carbon-carbon double bond (C=C).

The term "estomer" refers to an oligomeric fatty acid that contains secondary ester linkages on the alkyl backbone of the molecule. For example, estomers may be formed as a result of esterification of normal fatty acid by a hydroxy fatty acid. The term "estolide" has also been used to describe an oligomeric fatty acid that contains secondary ester linkages on the alkyl backbone of the molecule. However, the term "estomer" introduced here can be amended as discussed below using the standard nomenclature of polymer chemistry to provide a more specific molecular description. The term "estolide" can not be readily modified to convey any further information regarding molecular composition.

More specifically, the term "estomonomer" refers to compounds having the structure of Formula 1, in which the meanings of the variables are specified below in the application:

Formula 1

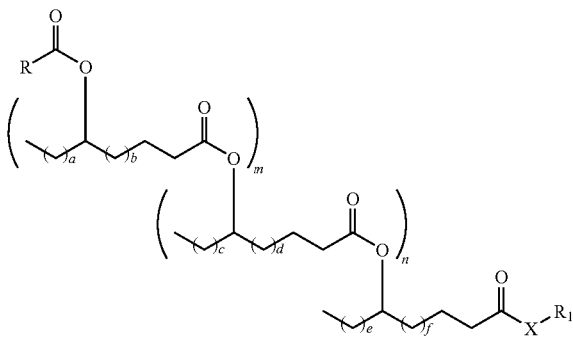

wherein R is a linear $C_1$-$C_{18}$ alkane such as a linear $C_5$-$C_{13}$ alkane, typically comprising the aliphatic portion of fatty acids such as hexanoic, octanoic, capric, lauric, or myristic acids; each of m and n is 0 or a positive integer; each of the sums (a+b) and (c+d)=1, 3, 5, 7, 9, 11, 13, or 15; (e+f)=9, 11, 13, or 15; X is $NR_2$, O or S; and each of $R_1$ and $R_2$ is a $C_1$-$C_{30}$ hydrocarbon that may contain linear, branched, saturated, unsaturated and/or aromatic functionalities. The estomonomer has one branch off main fatty acid backbone.

Further specificity may be conveyed through the terms "mono-estomer," "di-estomer," "tri-estomer," "oligo-estomer," "poly-estomer" and so forth, wherein the prefix indicates the number of secondary ester linkages contained in the molecule (excluding any secondary ester that may arise through a particular X—$R_1$ combination) and is called the "estomer degree" (ED), as distinct from estolide number EN). Thus, a compound where m+n=0 would be a mono-estomer, m+n=1 a di-estomer, and so forth. The prefixes do not place restrictions upon any of the variables a-f, or R and X—$R_1$.

The nomenclature developed above for molecules of the general composition given in Formula 1 may be readily extended to those species whose general composition is depicted in Formula 2. For molecules of the general structure given in Formula 2, where there are two secondary esters within the alkyl portion of the X—$R_1$ containing carboxylic acid derivative (known hereafter as the "backbone fatty acid"), the term "estodimer" is used.

The term "estodimer," more specifically, refers to compounds the structure of which includes the moiety of Formula 2, in which the meanings of the variables are specified below in the application:

Formula 2

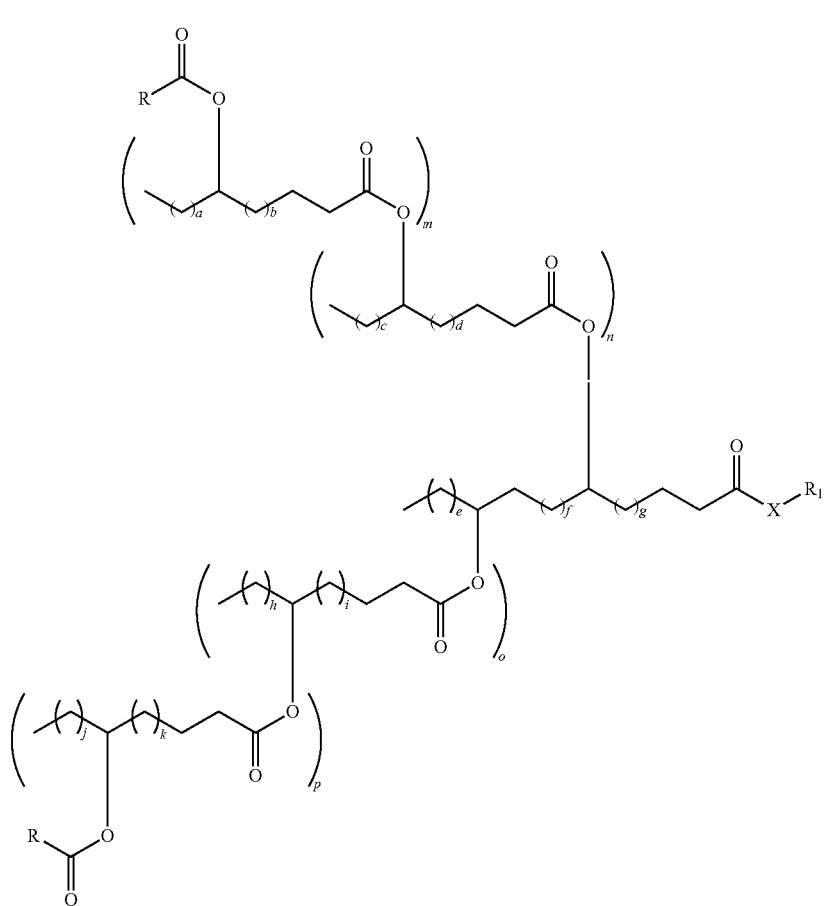

wherein R is a linear $C_1$-$C_{18}$ alkane, e.g., a linear $C_5$-$C_{13}$ alkane, typically comprising the aliphatic portion of fatty acids such as hexanoic, octanoic, capric, lauric, or myristic acids; each of m, n, p, and o is 0 or a positive integer; each of the sums (a+b), (c+d), (h+i) and (j+k) is 1, 3, 5, 7, 9, 11, 13, or 15; the sum (e+f+g) is selected from the group consisting of 7, 9, 11, 13, and 15; X is $NR_2$, O or S; and each of $R_1$ and $R_2$ is a $C_1$-$C_{30}$ hydrocarbon optionally containing linear branched, saturated, unsaturated and/or aromatic functionalities. The estodimer has two branches off the backbone fatty acid.

The prefixes discussed with regard to Formula 1 compositions may also be used in conjunction with "estodimer" and retain their direct relationship to the number of secondary ester linkages in the molecule (excluding any secondary ester that may arise through a particular $X$—$R_1$ combination). Thus, for $m+n=o+p=0$, the resultant molecule would be a "di-estodimer" reflecting the two RCOO-backbone fatty acid linkages. A "mono-estodimer" would simply be a "mono-estomer" as there is only one secondary ester linkage within the molecule.

The terms "symmetric" and "asymmetric" are used herein to provide further specificity. wherein a symmetric estodimer has $m+n=o+p$ and an asymmetric estodimer has $m+n\neq o+p$.

The term "fatty acids" refers to organic acids comprising a hydrocarbon chain that is at least four carbon atoms long.

The term "saturated" refers to organic molecules or moieties (e.g., hydrocarbon chains) which include exclusively carbon-carbon single bonds (i.e., $\alpha$-bonds) and contain no carbon-carbon double or triple bonds; the term "unsaturated" refers to organic molecules or moieties (e.g., hydrocarbon chains) which include at least one carbon-carbon double or triple bond.

The term "polyalphaolefins (PAO)" refers to synthetic hydrocarbons manufactured by cationic oligomerization of $C_8$-$C_{12}$ olefins, followed by hydrogenation and fractionation.

If any compound or moiety discussed below (e.g., hydrocarbons, alkyls, olefins, esters, etc.) is substituted, the substituents are independently selected from the group consisting of halogen, —OH, —SH, —$NH_2$, —CN, —$NO_2$, alkoxy, trihalomethyl, carbamoyl, aryl, arylalkyl or the like.

The terms "base stock" or "base oil" are interchangeable and are defined as a base compound, typically a fluid which makes up the majority of the lubricant formulation and possess inherent lubricating properties, which is commonly a refined petroleum fraction or a selected synthetic material, to be combined with additive(s) to produce a lubricant.

The term "a lubricant" is defined as a substance (often but not necessarily a liquid) introduced between two moving surfaces to reduce friction and wear between them. A lubricant provides a protective film which allows for two touching surfaces to be separated and "smoothed," thus lessening the friction between them. Lubricants chemically interact with surfaces so that contact only occurs with the smooth and free lubricant. By this process, abrasive particles are dissolved into the lubricant, thus making them also very good solvents and cleaners.

The term "ester" refers to an organic molecule or moiety having the —C(O)—O— functionality.

The term "effective amount" refers to any amount of a compound, e.g., an additive, that produces a measurable effect for the intended purpose. For example, an effective amount of an antiwear agent used in a lubricant composition is an amount that reduces wear in a machine by a measurable amount as compared with a composition that does not include the antiwear agent.

The term "pour point" (ASTM D-92) is the minimum temperature of a liquid, particularly a lubricant, after which, on decreasing the temperature, the liquid ceases to flow. It is a rough indication of the lowest temperature at which oil is readily pumpable. The term "pour point depressant" refers to compounds that lower that temperature.

We provide methods of obtaining the base stock which include the process of chemical modification of algal oil. In general, the methods provide for using algae as a starting material and include cultivation and harvesting of certain species of algae, followed by extracting algal oil, optional refining and purification of the extracted oil, and, final, by chemically modifying the oil.

Using algae for such purposes may prove beneficial, because algae are the cheapest, fastest growing, and highest yielding known biomass feedstocks. Most algae are eukaryotic, photosynthetic organisms that live in a wet environment. They are distinguished from the higher plants by a lack of true roots, stems or leaves. Many species are single-celled and microscopic (including phytoplankton and other microalgae). Algae's single-celled structure is extremely efficient in use of light and absorption of nutrients, even to such an extent that algae's growth and productivity may be 30 to 100 times higher than crops like soybeans.

Algae contain lipids and fatty acids as membrane components, storage products, metabolites and sources of energy. Algal strains, diatoms, and cyanobacteria (catagorized collectively as "microalgae") have been found to contain proportionally high levels of lipids (over 30%). Selection of the appropriates strain, optimum cultivation conditions, and genetic modification through directed evolution or metabolic engineering of the algae organism can enable the efficient production of mono- and polyunsaturated lipids, internal and alpha-olefins, and various other hydrocarbons.

These feedstock molecules can be used directly in the synthesis of estomer lubricant base stocks in the case of mono-unsaturated lipids or oleic acid or undergo intermediate steps to alter their chemical structure to obtain molecules that are useful as lubricants or precursors thereof. Examples of intermediate steps are partial hydrogenation or olefin metathesis. Additional and alternate chemical modification steps will be discussed below.

Cultivation systems that may be used for growing the algae can vary depending on the product or products and the strain of algae. Generally, algae may be grown according to known techniques. Closed bioreactors (also known as photobioreactors, or PBR) may be used to facilitate a monoculture tailored to the production of algae having a high percentage of fatty acids and an optimal distribution of unsaturated fatty acids. PBR are capable of providing each cell the precise conditions needed for maximum productivity.

One example of such a cultivation is described in published No. US 2007/0048848, which is incorporated herein by reference in its entirety, and which discloses a preferred method of culture and harvesting of algae in a closed system bioreactor. Alternatively, open systems may be also used as it has been demonstrated that such systems can result in very fast growing strains. Other methods of growing algae may be selected, if desired.

Algae that are suitable for the use in our methods have high levels of lipids and/or oil, typically higher than about 30 mass %, for example, as high as about 90 mass %. One example of a species of alga that may be used is *Botryococcus*, which is a known hydrocarbon producer. Under unfavorable conditions of growth, *Botryococcus* enters a stage in which its unsaponifiable lipid content increases to a level of about 90 mass %. The bulk of the *Botryococcus* hydrocarbon (about 95 mass %) is extracellularly located in the colony matrix and in occluded globules. A method for cultivation and production of *Botryococcus* described in US 2006/0252138 may be used, and is incorporated herein by reference in its entirety.

Some other representative usable algae that are germane include those listed in Table 1.

TABLE 1

| Strain | Protein | Carbohydrates | Lipids | Nucleic acid |
|---|---|---|---|---|
| Scenedesmus obliquus | 50-56 | 10-17 | 12-14 | 3-6 |
| Scenedesmus quadricauda | 47 | — | 1.9 | — |
| Scenedesmus dimorphus | 8-18 | 21-52 | 16-40 | — |
| Chlamydomonas rheinhardii | 48 | 17 | 21 | — |
| Chlorella vulgaris | 51-58 | 12-17 | 14-22 | 4-5 |
| Chlorella pyrenoidosa | 57 | 26 | 2 | — |
| Spirogyra sp. | 6-20 | 33-64 | 11-21 | — |
| Dunaliella bioculata | 49 | 4 | 8 | — |
| Dunaliella salina | 57 | 32 | 6 | — |
| Euglena gracilis | 39-61 | 14-18 | 14-20 | — |
| Prymnesium parvum | 28-45 | 25-33 | 22-38 | 1-2 |
| Tetraselmis maculata | 52 | 15 | 3 | — |
| Porphyridium cruentum | 28-39 | 40-57 | 9-14 | — |
| Spirulina platensis | 46-63 | 8-14 | 4-9 | 2-5 |
| Spirulina maxima | 60-71 | 13-16 | 6-7 | 3-4.5 |
| Synechoccus sp. | 63 | 15 | 11 | 5 |
| Anabaena cylindrica | 43-56 | 25-30 | 4-7 | — |

Certain strains of microalgae that are suitable for the use in our methods are shown in Table 2, where fatty acids are shown in bold and are present at a level of 15 mass % or higher. The bold figures separated by a column signify the number of carbons in the acid and the number of the sites of unsaturation; e.g., the notation "18:1" signifies a $C_{18}$ acid with one site of unsaturation (i.e., a double bond), and thus refers to oleic acid, i.e., the monounsaturated organic acid having the formula $CH_3-(CH_2)_7-CH=CH-(CH_2)_7-COOH$.

Yet other representative examples of oil producing algae that may be utilized in our methods include, without limitations, *Atractophora hypnoides* P.L.Crouan and H.M.Crouan (also known as "red algae"), *Ascophyllum nodosum*, *Charales* (also known as green algae), *Codium, Fucus, Haematococcus, Ulva lactuca, Laminaria, Lemanea, Macrocystis, Mastocarpus stellatus, Pelvetia canaliculata, Palmaria palmate, Porphyra*, and *Postelsia palmaeformis*.

TABLE 2

| Strain | Nitrogen-sufficient cells | Nitrogen-deficient cells |
|---|---|---|
| Ankistrodesmus | 16:0, 16:4, 18:1, 18:3 | 16:0, 18:1, 18:3 |
| Botryococcus braunii | 16:0, 18:1, 18:2, 18:3 | 16:0, 18:1, 18:3, 20:5 |
| Dunaliella bardawil | not determined | 12:0, 14:0/14:1, 16:0, 18:1, 18:2, 18:3 |
| Dunaliella salina | 14:0/14:1, 16:0, 16:3, 16:4, 18:2, 18:3 | 16:0, 16:3, 18:1, 18:2, 18:3 |
| Isochrysis sp. | 14:0/14:1, 16:0, 16:1, 18:1, 18:3, 18:4, 22:6 | 14:0/14:1, 18:1, 18:2, 18:3, 18:4, 22:6 |
| Nannochloris sp. | 14:0/14:1, 16:0, 16:1, 16:2, 16:3, 20:5 | not determined |
| Nitzschia sp. | 14:0/14:1, 16:0, 16:1, 16:2, 16:3, 20:6 | not determined |

If desired, a genetically modified strain of algae may be used or a strain that has been subjected to directed evolution, tailored in such a way as to obtain a preferred fatty acid or hydrocarbon product profile to reduce or remove the need for future additional separation steps, as well as for optimizing productivity and yield of the desired fatty acids or hydrocarbons.

Once an appropriate species of algae has been cultivated, it can be then harvested. Various harvesting methods may be employed as appropriate. Algae can be harvested using microscreens, by centrifugation, by flocculation or the like.

Froth flotation is another suitable method that may be used to harvest algae, whereby the water and algae are aerated into a froth, with the algae then removed from the water. Alum and ferric chloride are chemical flocculants used to harvest algae. Water that is more brackish, or saline may require additional chemical flocculent to induce flocculation. Harvesting by chemical flocculation is a method that may be too expensive for large operations. In such cases, interrupting the carbon dioxide supply to an algal system can cause algae to flocculate on its own, which is called "autoflocculation."

Chitosin, commonly commercially used for water purification, may also be used as a flocculent. The shells of crustaceans are ground into powder and processed to acquire chitin, a polysaccharide found in the shells, from which chitosin is derived. Ultrasound based methods of algae harvesting are currently under development and may be used, and other, additional methods are currently being developed.

The algae cultivated and harvested as described above are then subjected to the process of extraction to obtain oils contained therein. A variety of methods may be used to extract the algal oil. Regardless of which method of extraction is used, the algal oil does not undergo chemical modification during extraction. The simplest method is mechanical crushing. Since different strains of algae vary widely in their physical attributes, various press configurations (screw, expeller, piston or the like) work better for specific algae types.

Often, mechanical crushing is used in conjunction with chemicals, such as benzene and ether. Oil can also be separated by hexane extraction, which is widely used in the food industry and is relatively inexpensive. For instance, Soxhlet extraction may be used to carry out the process of extraction, whereby oils from the algae are extracted through repeated washing, or percolation, with an organic solvent such as hexane or petroleum ether, under reflux in specialized glassware.

Alternatively, enzymatic extraction may be used, i.e., the process that uses enzymes to degrade the cell walls, with water acting as the solvent, thus facilitating fractionation of the oil. The enzymatic extraction may be assisted by ultrasonication. The combination "sonoenzymatic treatment" may cause faster extraction and higher oil yields.

Other alternative extraction methods include expression/expeller press, osmotic shock, the use of supercritical fluid, the above mentioned ultrasound-assisted extraction, and other methods, e.g., methods directed to extraction of specific types of oils, such as those with a high production of long-chain highly unsaturated fatty acids. For example, expression/expeller press process is based on the phenomenon that when algae is dried it retains its oil content, which then can be "pressed" out with an oil press. Commercial manufacturers of vegetable oil often use a combination of mechanical pressing and chemical solvents in extracting oil.

In the osmotic shock procedure, a sudden reduction in osmotic pressure, can cause cells in a solution to rupture. Osmotic shock is sometimes used to release cellular components, such as oil. In the supercritical fluid procedure, $CO_2$ is liquefied under pressure and heated to the point that it has the properties of both a liquid and a gas. This liquefied fluid then acts as the solvent in extracting the oil. Finally, in the process of ultrasonic extraction, ultrasonic waves are used to create cavitation bubbles in a solvent material. When these bubbles collapse near the cell walls, shock waves and liquid jets are created causing those cells walls to break and release their contents comprising oil into the solvent.

Following the above-described process of extraction, the so extracted algal oil may be optionally refined and/or purified. Various known methods of refinement and/or purification may be used, including the methods suitable for refining vegetable oils and byproducts thereof, as described in U.S. Pat. No. 6,172,247, the subject matter of which is incorporated herein by reference in its entirety.

Some exemplary methods of refinement and/or purification that may be used include a process of natural oil deodorization, which typically involves a steam stripping process, wherein steam is contacted with vegetable oil in a distillation apparatus operating at low pressure and a temperature sufficient to vaporize objectionable volatile impurities at the operating pressure.

This process, commonly known as "vacuum-steam deodorization," relies upon volatility differences between the vegetable oil and as many as 60 impurities, to strip the relatively more volatile impurities from the relatively less volatile vegetable oil. Vacuum-steam deodorization treatment also beneficially decomposes peroxides in the vegetable oil and removes other volatile compounds that may result from such decomposition.

The extracted and optionally refined and/or purified algal oil is then subjected to further chemical modification that can be carried out in a variety of ways, typically, yielding a mixture of saturated and unsaturated fatty acids. As a result of chemical modification, a beneficially broad range of highly branched and saturated molecular structures for use as a lubricant base stock or additive may be eventually obtained.

The separated fatty acid groups such as that of oleic acid may also be used as the starting material for creating compounds having estomer moieities. Different fatty acids may also be separated or blended to create a mixture with desirable fatty acid profile for the building blocks of the algal oil additive or base oil.

Various methods of chemical modification of algal oil may be used. Chemical modification of algal oil may be carried out via the formation of estomers, for example, estomers having the general structures of Formulae 1 or 2, as discussed below in more detail. Other types of estomers may be useful, if desired. Alternative methods may be used for chemical modification of algal oil to produce products that have desirable lubricant properties as discussed below.

In general, the molecular compositions of the base stocks described herein are chosen to give optimal lubricant properties. These properties include but are not limited to pour point, viscosity, viscosity index (VI), film forming abilities, volatility, boiling points of narrow range, and good oxidative stability.

To achieve the above-discussed beneficial properties, algal oil may be chemically modified to obtain an estomonomer having the general structure given in Formula 1:

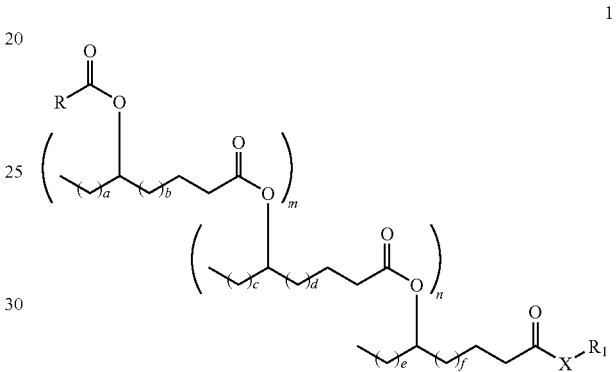

wherein R is a linear $C_1$-$C_{18}$ alkane such as a linear $C_5$-$C_{13}$ alkane, typically comprising the aliphatic portion of fatty acids such as hexanoic, octanoic, capric, lauric, or myristic acids; each of m and n is 0 or a positive integer; each of the sums (a+b) and (c+d)=1, 3, 5, 7, 9, 11, 13, or 15; (e+f)=9, 11, 13, or 15; X is $NR_2$, O or S; and each of $R_1$ and $R_2$ is a $C_1$-$C_{30}$ hydrocarbon that may contain linear, branched, saturated, unsaturated and/or aromatic functionalities.

In some other aspects, algal oil may be chemically modified to obtain an estodimer having the general structure given in Formula 2:

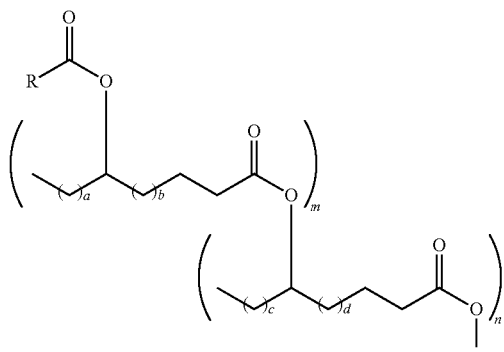

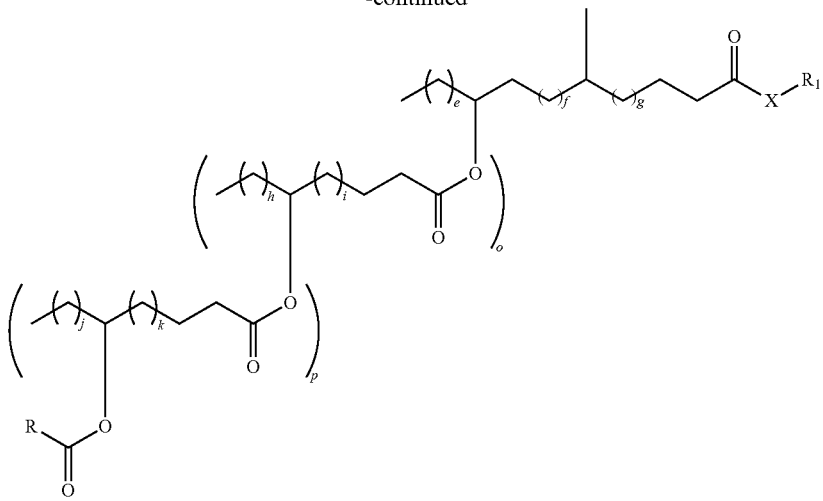

wherein R is a linear $C_1$-$C_{18}$ alkane, e.g., a linear $C_5$-$C_{13}$ alkane, typically comprising the aliphatic portion of fatty acids such as hexanoic, octanoic, capric, lauric, or myristic acids; each of m, n, p, and o is 0 or a positive integer; each of the sums (a+b), (c+d), (h+i) and (j+k) is 1, 3, 5, 7, 9, 11, 13, or 15; the sum (e+f+g) is selected from the group consisting of 7, 9, 11, 13, and 15; X is $NR_2$, O or S; and each of $R_1$ and $R_2$ is a $C_1$-$C_{30}$ hydrocarbon optionally containing linear, branched, saturated, unsaturated and/or aromatic functionalities.

The general estomonomer structure given in Formula 1 has excellent VI, low pour point and good oxidative stability. The compositions may comprise a distribution of estomonomer structures as encompassed by the variables indicated in Formula 1. The range of variables a+b, c+d, and e+f may result from the choice of starting fatty acid and may be chosen to give an overall even number of carbons in the fatty acid hydrocarbon tail.

The individual values of the variables in a given sum results from the linkage position of the secondary ester and is typically centered around the initial position of the alkene in the starting fatty acid. For instance, taking oleic acid to be the fatty acid detailed by variables e and f indicates that e+f is 13 and the range for e is maximal near 7-8 while f is centered around 5-6 since the C=C double bond occurs between $C_9$ and $C_{10}$ in oleic acid. A similar evaluation gives e+f=11 with e maximal value is near 5-6 and f maximal value is near 5-6 for palmitoleic acid.

While the values of the variables are centered around the location of the olefin in the starting fatty acid derived from algal oil, they may vary due to isomerization that occurs during the formation of the secondary estomer ester bond. The secondary ester bond itself is known to have good oxidative stability and imparts this stability upon the molecule as a whole. Thus, the position of the bond is indicated in Formula 1 to be secondary in nature.

The extent of oligomerization in the estomer is indicated by the variables m and n. The extent of oligomerization affects properties such as viscosity, boiling point, volatility, and VI, with the boiling point, volatility, and viscosity increasing with larger values of m and n. For low viscosity base stocks, the desired range of molecular weights of the estomer are encompassed through m and n ranging between 0 and 2. If the estomer is used as a viscosity modifier or in a high viscosity lubricant product, the desired molecular weights are typically higher and can be described by m and n ranging from 0 to 5 with m+n>1. For a composition containing a distribution of estomers, m and n need not be integers. The nature of the R group in the capping carboxylic acid is chosen to maintain or increase the oxidative stability of the composition and is typically comprised of a saturated hydrocarbon.

The length and branching ratio of the saturated hydrocarbon may be chosen to maintain or decrease the pour point of the base stock composition. Typical lengths may be from $C_1$ to $C_{17}$ with a branching ratio<0.3. The X—$R_1$ group is chosen to maintain the desired properties of the estomer as either a base stock or viscosity modifier with particular attention paid to the effects on oxidative stability and viscosity. As such, the X—$R_1$ group can be selected from amines, thiols and alcohols with $R_1$ (and $R_2$ in the case of amines) chosen from $C_1$-$C_{30}$.

The polar nature of X—$R_1$ in tandem with the secondary estomer ester groups can be exploited to favorably affect the film forming and metal affinity of the basestock with different X—$R_1$ groups used in different lubricating applications. The estodimer depicted in Formula 2 differs from the estomonomer in that the foundation fatty acid detailed by variables e, f, and g is either a di-unsaturated fatty acid such as linoleic acid, or derived from partial hydrogenation of a polyunsaturated fatty acids. Examples of the latter include but are not limited to linolenic, eicosapentaenoic and arachidonic acids. The remaining portions of the molecule can be described as above for the estomonomer.

With regard to the above-mentioned synthetic process of forming estomers from the algal oil, the estomers may now be synthesized from vegetable oils and may be used as ingredients in various industrial fields such as cosmetics, coatings, biodegradable lubricants and the like. They are commonly synthesized from oleic acid warmed with perchloric or sulfuric acid. The average number of fatty acid units added to the first base fatty acid (i.e., "the estomer degree") can vary as a function of reaction temperature. The secondary ester linkages are more resistant to hydrolysis than those of triglycerides, and the unique structure of the estomer results in materials having far superior physical properties than mineral oils and vegetable and petroleum-based oils.

Estomers made from vegetal oils have a good oxidative stability and low-temperature properties. Oxidative stability may be improved in removing the unsaturation of oleic acid and low-temperature performance may be improved in using oleic acid and various short or middle-chain saturated fatty acids (e.g., lauric or myristic acid or coconut oil).

In one example of the process of chemical modification of algal oil via the formation of estomers, a high oleic content algal oil may be combined with one or more predominantly saturated fatty acid(s), such as $C_8$ to $C_{20}$ saturated fatty acid(s), for example, $C_{12}$-$C_{16}$ saturated fatty acid(s). The saturated fatty acid(s) may be obtained from a variety of sources, such as algal oil, animal tallow, and vegetable oils.

The algal oil and saturated fatty acid(s) may be then reacted to form an adduct. This reaction is a first synthetic step in the process of estomer formation and may be catalyzed by a variety of acids, including both Lewis and protic acids. Examples of Lewis acids that may be used include, without limitation, boron trifluoride, aluminum trichloride, tin tetrachloride, zinc dichloride and lanthanide trichloride (where lanthanide is an element in the lanthanide series). Protic acids that may be used include, without limitation, mineral acids such as perchloric or sulfuric acids or sulfonic acids such as toluenesulfonic and methanesulfonic acids. In the example, perchloric acid is used.

The algal oil/saturated fatty acid(s) ratio (molar) may range from about 1:4 to about 4:1, such as about 1:2 to about 2:1, for example, about 1:1. The process of the formation of estomers may be designed to obtain mono-, di-, or poly-estomers. For example, the use of estodimers, i.e., estomers with 2 branches off of the main fatty acid backbone, allow for the efficient use of linoleic acid in the production of saturated hydrocarbon structures. They also can allow for novel molecular formulations that can have exceptional cold flow and viscosity index properties depending on the raw components used. High molecular weight compounds can be produced for use in high viscosity lubricant applications.

Estomers that result from the acid catalyzed reaction discussed above may have free carboxylic acid groups that may be further reacted with an alcohol, thiol, or amine to form an ester, thioester, or amide. In addition to the acid catalysts mentioned above, this reaction may be alternatively catalyzed by a basic catalyst such as potassium or sodium hydroxide. The alcohol, thiol, or amine that may be used includes any of $C_1$-$C_{12}$ alcohols, thiols, and amines. In the preferred embodiment, a branched alcohol with branching occurring at the $C_1$ and or $C_2$ position, for example, isopropyl or 2-ethylhexyl alcohols is used.

The estomer formation reaction may be further illustrated by one exemplary synthetic scheme I:

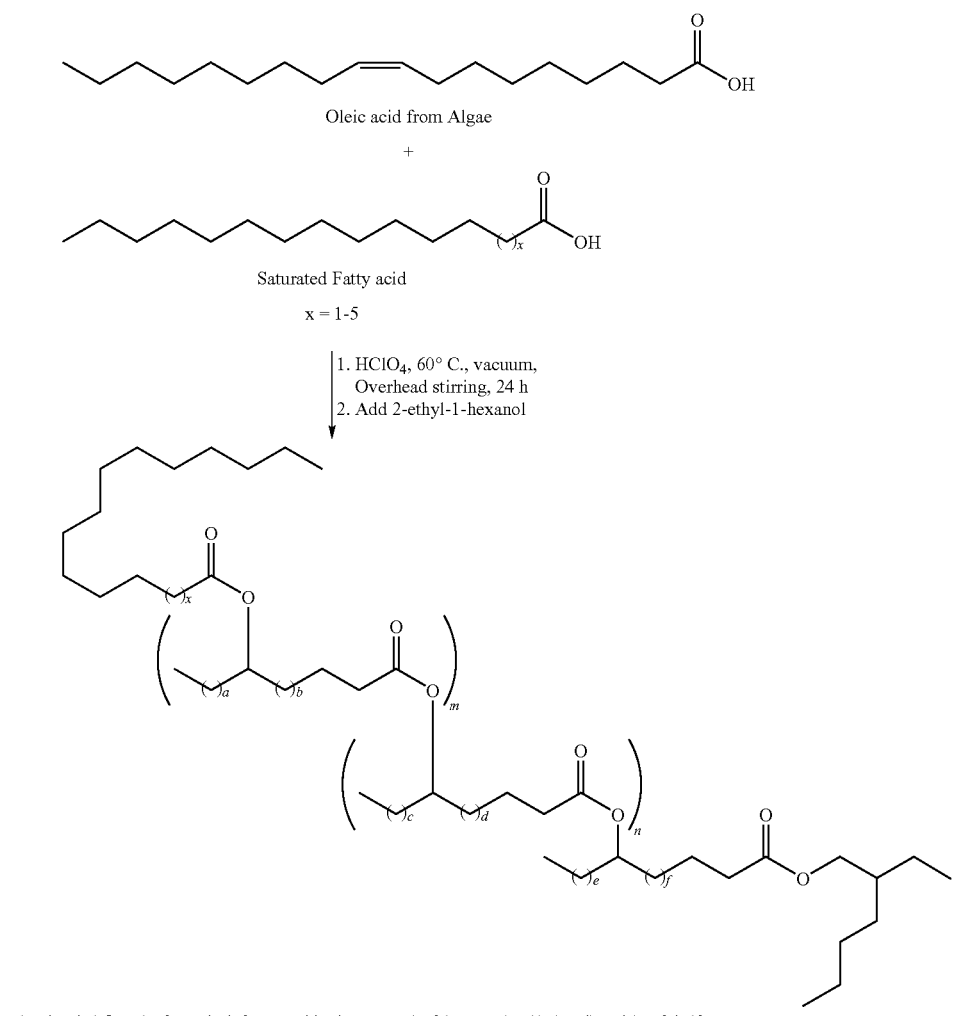

wherein x is 1-5; each of m and n is 0 or a positive integer; each of the sums (a + b), (c + d), and (e + f) is 13.

The process of formation of estomers from algal oil is further illustrated by FIG. 1, schematically demonstrating one aspect of the process. As can be seen, algal oil and unsaturated natural oil (8) are subjected to a refining and purification in process module 1, and are directed to the reactor module 2. In reactor module 2 the acid catalyzed estomer formation reaction occurs with a mixture of saturated (6) and unsaturated oils (8). The resulting product can be further reacted with an alchohol (7) to form an ester in module 3, catalyzed by either an acid catalyst as in reactor module 3 or a basic catalyst. Excess alchohol, monomer, and side products are removed by fractionation and distillation in process module 4. Other methods of chemical modification of algal oil may also yield useful lubricant basestocks, and precursors. Such exemplary methods as hydrogenation and partial hydrogenation, oligomerization of biologically produced α- and internal olefins, epoxidation, olefin metathesis, alkylarylation, cyclization, acetylation, oxidative scission, carboxylation, or transesterification may be used as an alternative to the estomer synthesis.

Hydrogenation is the addition of hydrogen to unsaturated organic compounds such as alkenes to afford alkanes or to aldehydes to afford alcohols. Hydrogenation reactions use metal catalysts, often those composed of platinum or similar precious metals.

To illustrate further, the addition of hydrogen to an alkene affords an alkane in a typical reaction:

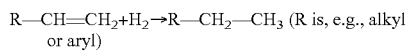

R—CH=CH$_2$+H$_2$→R—CH$_2$—CH$_3$ (R is, e.g., alkyl or aryl)

Both homogeneous and heterogeneous processes of alkene and alkyne hydrogenations are often characterized by the "Markovnikoff's rule," i.e., hydrogen addition takes place with syn addition, i.e., with hydrogen entering from the least hindered side. Partial hydrogenation is often used to improve thermal-oxidative stability while minimally impacting freezing points. Heterogeneous metal catalysts may be able to selectively convert polyunsaturated compounds typically found in natural oils into more desirable mono- and di-unsaturated compounds with limited formation of saturated compounds, transisomers, and conjugated dienes. U.S. Pat. No. 4,229,361, the disclosure of which is incorporated herein by reference in its entirety, discloses one such invention, a nitrogen-containing nickel catalyst for selective hydrogenation.

Another alternative method of chemical modification of algal oil, i.e., oligomerization of biologically produced α- and internal olefins takes advantage of producing internal and alpha olefins through a bio-transformation in genetically modified algae strains, and thus opens the possibility of more conventional synthetic lubricant basestocks such as PAO and PIO(i.e., poly internal olefin). These can be manufactured by the oligomerization of internal n-olefins or α-olefins using traditional Ziegler type catalysts and other known methods.

The method of epoxidation may be used as the most convenient known method of removing double bonds. Olefin peroxidation involves oxidation of an olefin with a peroxide, usually a peroxyacid. For triacylglycerol usually performic or peracetic acid are most common resulting in formation of oxirane rings at double bond sites.

Another alternative method of chemical modification of algal oil, i.e., olefin metathesis, allows conversion of all unsaturated acyls to saturated acyls in a triacylglycerol and, unfortunately, leads to solid products. The problem may be solved by getting lower (i.e., C$_8$-C$_{10}$) saturated acyls. This can be done by olefin metathesis reaction followed by hydrogenation. For example, co-metathesis of oleic ester with short chain olefins such as ethene results in an unsaturated ester with chain lengths C$_{10}$ and the corresponding alpha-olefin. The alpha-olefins may then be reacted to form PAO using known commercial methods. Furthermore, the unsaturated acyls can be completely hydrogenated to saturated acyl chain length of approximately C$_{10}$, in presence of 10% palladium on carbon in dichloromethane, or epoxidized to remove unsaturation.

Another alternative method of chemical modification of algal oil, i.e., alkylarylation is based on Friedel-Craft addition of phenols and alkylaromatics to the double bonds of algal oil/fatty acid ester to afford alkylaryl derivatives with improved thermo-oxidative stability and decreased freezing points. Side reactions (e.g., polymerization of acid and oils to dimer or trimer derivatives) may need to be addressed.

Cyclization is an option allowing elimination of unsaturation sites. Dimerization by Diels-Alder reaction leads to formation of cyclic structures. This is frequently done commercially with highly unsaturated oils (SBO, linseed, sun flower) to give products that are base materials for plasticizers, alkyl resins, and stabilizers.

The method of acetylation may be useful for algal oils containing hydroxyl group, typically yielding the products having high viscosity index and low freezing point, but poor thermo-oxidative stability.

The method of oxidative scission removes double bonds through oxidative scission. These can be converted to diesters after esterification. One potential mechanism of oxidative scission (ozonolysis) is shown on the reaction scheme II.

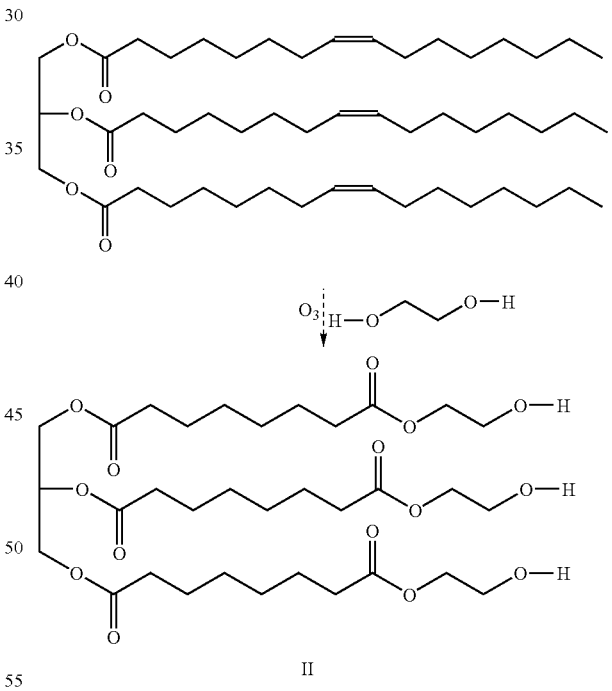

II

Another alternative method of chemical modification of algal oil that may be used is carboxylation of one of the following three types: hydroformylation (oxosynthesis), hydrocarboxylation (Reppe reaction) and Koch synthesis. The carbon chain undergoes rearrangement as the result of carbonium ion isomerization, yielding a mixture of isomers with high proportions of branched dicarboxylic esters.

A further method of chemical modification of algal oil is the Oligomerization of Olefins from Syngas. Algal oil feedstock can be converted to synthesis gas through a gasification process such as described in U.S. Pat. No. 6,251,148 'Process for producing synthetic gasses'. Ethylene can then be derived through several routes from a synthesis gas mixture of carbon monoxide monoxide+hydrogen (syngas) as described in U.S. Pat. No. 4,270,015. Alpha-olefins and PAO can then be produced from the ethylene using the commercial methods.

Yet a further method of chemical modification of algal oil is the synthesis of Polyalpha-olefins from higher fatty acids. US 2007/0299291 A1 describes a multistep process applicable to fatty acids from algal oil where, in the first step, a feedstock comprising fatty acids is transformed to esters, in the second step the esters catalytically hydrogenated to form fatty alcohols, in the third step the fatty alcohols in turn are dehydrogenated to alpha-olefins, in the fourth step the obtained alpha-olefins are converted to branched hydrocarbons by contacting them either with a homogeneous or heterogeneous oligomerisation catalyst, and in the fifth step the obtained oligomers are hydrogenated to produce thermally stable base oils or base oil components.

Finally, another alternative method of chemical modification of algal oil that may be used is transesterfication. Animal and plant fats and oils are typically made of triglycerides which are esters of free fatty acids with the trihydric alcohol, glycerol. In the transesterification process, the alcohol is deprotonated with a base to make it a stronger nucleophile. Commonly, ethanol or methanol is used. The reaction needs no inputs other than the triglyceride and the alcohol. Transesterification of partially hydrogenated or cyclized ester natural oils are important because these reactions yield monoesters with better thermal stability and lower freezing points than the natural triglyceride. Most transesterfied products are produced using the well known base-catalyzed techniques as it is the most economical process requiring only low temperatures and pressures and producing over 98% conversion yield (provided the starting oil is low in moisture and free fatty acids).

The chemically modified algal oils, obtained as described above, have valuable properties making them suitable as base stocks for preparing environmentally friendly lubricant compositions useful in a variety of applications, such as crankcase oils, hydraulic fluids, drilling fluids, two-cycle engine oils, penetrating oils, fuel additives, greases, brake fluids, shock absorber fluids, metal working fluids, pump oils, mining and conveyor lubricants, compressor oils, heat transfer liquids, dielectric fluids, off-shore drilling lubricants, space applications, turbine oils, and other formulations that benefit from the superior fluid properties and thermal stability provided by the chemically modified algal oils of this invention.

When used as a base stock, chemically modified algal oil can be mixed with an effective amount of other lubricating base oils including, but not limited to, mineral oils, vegetable oils, other estomers, polyalphaolefins, polyol esters, oleates, diesters, etc.

Generally, to prepare biodegradable lubricant compositions, the chemically modified algal oils, serving as a base stock, may be mixed with an effective amount of at least one additive. Any of a variety of conventional lubricant additives may be so used to serve as detergents, anti-wear agents, antioxidants (i.e., oxidation inhibitors), viscosity index improvers, dispersants, pour point depressants, corrosion protectors (i.e., corrosion inhibitors), friction coefficient modifiers, metal deactivators, compatibility agents, colorants, extreme pressure additives, antifoam agents, defoamants, demulsifiers and the like. The concentration of the chemically modified algal oils, serving as a base stock, may be between about 60 mass % and about 95 mass %, based on the weight of the entire composition.

The chemically modified algal oils may serve not only as a base stock but optionally also as additives. If they are used as additives, they may comprise between about 5 mass % and about 30 mass %, based on the weight of the entire composition.

The chemically modified algal oils are capable of meeting or exceeding the performance, economical, and environmental requirements of current lubricant products. The CMAO can be utilized as the base for a renewable and/or biodegradable lubricant in a variety of applications, such as crankcase oils, hydraulic fluids, drilling fluids, two-cycle engine oils, penetrating oils, fuel additives and the like. In addition to the environmental aspects the CMAO can add improved performance in other critical areas of fluid performance in these applications, such as VI, volatility, corrosion, wear protection, and the like. A particular high performance application may be an engine oil product that can take advantage of many of the benefits of the CMAO, and may, therefore, be used in motor oil formulations, either to make a base stock or as an additive, depending on the desired amount of renewable content to be blended into the formulation and on other design requirements.

For the chemically modified algal oil to be used in a motor oil formulation, it must be tailored through the chemical modification process to meet the demands of the application. In particular, it is necessary to create modified molecules that have the correct molecular weight and viscosity characteristics for the motor oil formulation. For example, a CMAO to be used as the base oil in a 5W-30 motor oil formulation may have a viscosity of between 2 and 10 at 100 C and excellent cold flow characteristics. The CMAO can be the sole base oil for the formulation or be a part of a base oil blend to make up the formulation. The other constituents of the base oil can be a blend from one to many different petroleum based oils that are a part of the API Base Stock groups and bio-based oil components.

The base oils are combined with an additive package to meet the rigorous demands of the motor oil application. These specific additives cause a motor oils life cycle to be extended and/or reduce the rate at which undesirable changes take place while others improve properties already present in the base oil. The key additive technologies used are pour point depressants, viscosity index improvers, detergents, dispersants, anti-foam agents, rust and corrosion inhibitors, oxidation inhibitors, and anti-wear additives. These additives must be designed to work well with the CMAO and other base oils components. The amounts and types of the additives to be used are not specified but are known in the motor oil art.

The above discussion focused on the use of the CMAO in a motor oil formulation that is typical of a 4 cycle or diesel engine technology typically used in modern automobiles. Another significant use for lubricants is for the lubrication of 2 stroke engines. 2 stroke engine oil formulations should meet many of the same design considerations as discussed above but the operating environment and performance requirements are typically not as stringent in this application because the oil is burned in the combustion chamber. The CMAO can serve as the base oil for in the 2 stroke application and have tremendous environmental benefits due to the lack of contaminants in the molecules.

Another use for the CMAO is as the base oil for a penetrating oil formulation. In addition to having excellent penetrating properties, the benefits of such biodegradable penetrating lubricants also include film forming capacity, corrosion inhibition, extended low temperature fluidity, high temperature viscosity, thermo-oxidative stability and extended shelf life and resistance to microbial or bacterial attack.

In some examples, a biodegradable penetrating lubricant may include:
 (a) between about 20 mass % and about 90 mass % of a biodegradable base oil, such as a natural or chemically modified algae, vegetable or animal oil.
 (b) between about 0.1 mass % and about 4 mass % (based on the weight of the entire composition) of at least an antioxidant providing oxidative stability and an organic solvent (e.g., any of ethyl lactate, a soy methyl ester, or at least one mineral spirit, or combinations thereof).
   optionally any of: wear inhibitor, corrosion inhibitor, pour point depressant, food grade tackifier, Turning to the particular above-mentioned additives that may be present in the motor oil or penetrating lubricant or any other mentioned lubricant product formulations, a wide variety of antioxidants may be used, such as hindered phenols, aromatic amines, alkaline earl metal salts of alkylphenolthioesters having preferably $C_6$ to $C_{12}$ alkyl side chains, calcium nonylphenol sulfides, ashless oil soluble phenates and sulfurized phenates, phosphosulfurized or sulfurized hydrocarbons, phosphorus esters, metal thiocarbamates and oil-soluble copper compounds as described in U.S. Pat. No. 4,867,890. They may be used individually by type or in combination with one another. The phenolic antioxidants, if used, may be ashless (metal-free) phenolic compounds or neutral or basic metal salts of certain phenolic compounds. Typical phenolic antioxidant compounds are the hindered phenolics which are the ones which contain a sterically hindered hydroxyl group, and these include those derivatives of dihydroxy aryl compounds in which the hydroxyl groups are in the o- or p-position to each other.

Typical phenolic antioxidants that may be used include the hindered phenols substituted with $C_6$ or longer alkyl groups and the alkylene coupled derivatives of these hindered phenols. Examples of specific phenolic materials of this type include 2-tert-butyl-4-heptyl phenol; 2-tert-butyl-4-octyl phenol; 2-tert-butyl-4-dodecyl phenol; 2,6-di-tert-butyl-4-heptyl phenol; 2,6-di-tert-butyl-4-dodecyl phenol; 2-methyl-6-di-tert-butyl-4-heptyl phenol; 2-methyl-6-di-tert-butyl-4-dodecyl phenol; or ortho coupled phenols such as 2,2'-bis(6-tert-butyl-4-heptyl phenol); 2,2'-bis(6-tert-butyl-4-octyl phenol); and 2,2'-bis(6-tert-butyl-4-dodecyl phenol).

Typical examples of the amino type antioxidants that may be used include: alkylated and non-alkylated aromatic amines such as the aromatic monoamines of the formula $R^3R^4R^5N$, where $R^3$ is an aliphatic, aromatic or substituted aromatic group, $R^4$ is an aromatic or a substituted aromatic group, and $R^5$ is H, alkyl, aryl or $R^6 S(O)_x R^7$ where $R^6$ is an alkylene, alkenylene, or aralkylene group, $R^7$ is a higher alkyl group, or an alkenyl, aryl, oralkaryl group, and x is 0, 1 or 2. The aliphatic group $R^3$ may contain from 1 to about 20 carbon atoms, for example, from 6 to 12 carbon atoms. The aliphatic group is a saturated aliphatic group.

Both $R^3$ and $R^4$ may be aromatic or substituted aromatic groups, and the aromatic group may be a fused ring aromatic group such as naphthyl. Aromatic groups $R^3$ and $R^4$ may be joined together with other groups such as S. Typical aromatic amines antioxidants have alkyl substituent groups of at least 6 carbon atoms. Examples of aliphatic groups include hexyl, heptyl, octyl, nonyl, and decyl. Generally, the aliphatic groups will not contain more than 14 carbon atoms. The general types of amine antioxidants useful in the present compositions include diphenyl amines, phenyl naphthylamines, phenothiazines, imidodibenzyls and diphenyl phenylene diamines. Mixtures of two or more aromatic amines are also useful. Polymeric amine antioxidants can also be used. Particular examples of aromatic amine antioxidants useful in the present invention include: p,p'-dioctyidiphenylamine; octylphenyl-β-naphthylamine; tert-octylphenyl-α-naphthylamine; phenyl-α-naphthylamine; phenyl-β-naphthylamine; p-octylphenyl-α-naphthylamine; 4-octylphenyl-1-octyl-β-naphthylamine.

Examples of suitable antiwear inhibitors that may be used include, but are not limited to, zinc dialkyl dithiophosphates, such as zinc di(isohexyl)dithiophosphate, which may be added to the present compositions to increase film thickness in elastohydrodynamic conditions, the additional effect of the additive which is desirable under severe operational conditions.

Examples of suitable corrosion inhibitors that may be used include, but are not limited to, nonionic polyoxyalkylene polyols and esters thereof polyoxyalkylene phenols, and anionic alkyl sulfonic acids.

Pour point depressants (also known as PPDs) are polymers that are designed to control wax crystal formation in lubricants resulting in lower pour point and improved low temperature flow performance. These wax-like molecules are soluble at ambient temperatures above freezing, but crystallize at lower temperatures and cause oil circulation problems. Only a small amount of PPD, such as less than about 0.5 mass % of the entire composition, is required in the present invention due to the use of highly refined base oils that do not have a high wax content and are designed to be able to maintain their viscosity characteristics at very low temperatures. Examples of suitable pour point depressants that may be used include, but are not limited to, C8 to C18 dialkyl fumarate/vinyl acetate copolymers, polyalkylmethacrylates and the like.

Some applications and environmental conditions may require an additional tacky surface film that protects equipment from corrosion. The tackifier also holds the lubricant to the surface of the moving parts and improves anti-wear. In this case, the tackifier is 1 to 2 weight percent of the lubricant. However, the tackifier can be from about 0.5 to about 5 weight percent. An example of a food grade tackifier that can be used in this invention is Functional V-584 Natural Rubber Tackifier for Fatty-Oil Based Lubricants/Food Grade, which is available from Functional Products, Inc., Macedonia, Ohio.

Our chemically modified algal oils may be also used as fuel additives. It is well known that the low temperature flow properties of waxy distillate fuels can be improved by employing wax crystal modifiers as additives to fuels in a manner functionally similar to waxy lube PPD. The use of such additives to distillate fuels avoids the more costly step of deep dewaxing of the distillate feedstock.

When mixed with diesel fuels or aviation fuels containing hydrocarbons that normally form wax crystals at low temperature, our chemically modified algal oils modify and depress the temperature at which wax crystals form, and minimize wax formation in the fuel. Accordingly, our chemically modified algal oils may be added to mineral oils and synthetic oils in quantities of less than about 1 mass %, based on the weight of the entire composition. As a result, the low temperature pour point of such fuels may be reduced more significantly than what is possible to achieve using known pour point depressants.

We now turn briefly to characterization of the performance of a base stock based on chemically modified algal oils in comparison to petroleum derived base oils and other biobased oils. The primary advantages of the CMAO are its biodegradability, high viscosity index (VI), low-temperature properties, volatility, and oxidative stability. These properties allow the CMAO to be formulated into a wide range of lubricant products as described above.

The comparative data on viscosities and the VI are provided in Table 3. As can be seen from the data presented in Table 3, the CMAO possess at least comparable, and in many cases superior VI characteristics. The same conclusion applies to biodegradability, the data on which are provided in Table 4.

TABLE 3

Comparative Data on Viscosities and Viscosity Indices

| Property, units (test method) | Group I Mineral Oil | Canola oil | Soybean Oil | PAO 8 | Polyol Ester(TMP) | CMAO Monoestomer |
|---|---|---|---|---|---|---|
| Viscosity at 40 0 C. (ASTM D 445) | 58 | 38.5 | 33 | 46.3 | 46.8 | 4.5-150 |
| Viscosity at 100 0 C. (ASTM D 445) | 8.2 | 8.5 | 7.8 | 7.74 | 9.4 | 2-12 |
| VI (ASTM D 2270) | 110 | 207 | 217 | 136 | 190 | 120-245 |

TABLE 4

Comparative Data on Biodegradability

| Property, units (test method) | CMAO Monoestomer | Vegetable oil | PAO | Mineral Oil | Polyol ester |
|---|---|---|---|---|---|
| Modified Sturm test % in 28 days (OECD 301 B) | 50-99% | 70-100% | 20-60% | 20-40% | 20-99% |

Key low temperature properties are compared in Table 5.

TABLE 5

Comparative Data on Low Temperature Properties

| Property, units (test method) | CMAO Monoestomer | Group I Mineral Oil | Canola oil | PAO 8 | Polyol Ester(TMP) |
|---|---|---|---|---|---|
| Pour Point, ° C. (ASTM D 97) | −20--45 | −12 | −18 | −57 | −39 |
| Cold Stoarage at −25° C., (days) | 7+ | <1 | <1 | 7+ | <1 |

As can be seen, the estomer has significantly better low temperature properties than vegetable and mineral oils and compares favorable with PAO and Esters of similar viscosities.

Volatility is an important property for lubricant vapor pressure, flammability, volatile burnoff and emissions. Volatility relates to the flash point, which is measured using Cleveland Open Cup test method. Micro oxidation data allows quantification of the volatility at particular temperatures, in this case 150° C. Key volatility properties are compared in Table 6.

As can be seen from the data provided in Table 6, the CMAOs are much less volatile than base oils of a similar viscosity.

Figure 2:
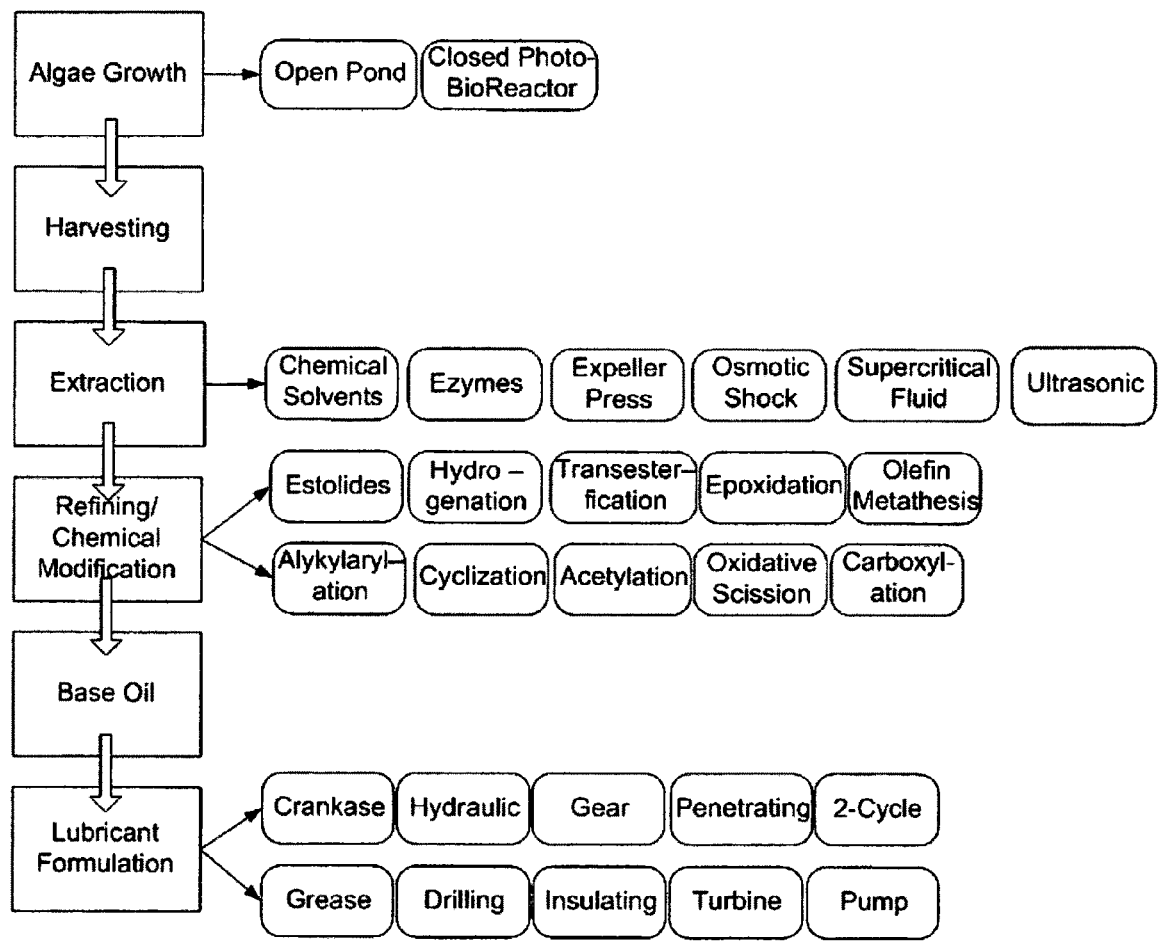
FIG. 2 is schematic illustration of a process of chemical modification of algal oil

The entire process of production of oleic estomers from algal oil is further illustrated by the schematic diagram shown by FIG. 2, which also shows some optional steps that may be used.

EXAMPLES

The following examples are provided to further illustrate the advantages and features of our materials and methods, but are not intended to limit the scope of this disclosure.

Example 1

Chemical Modification of Algal Oil

In an evacuated 1 L three-neck round bottom flask equipped with overhead stirrer, about 170 g (708 mmol) of high oleic content algal oil were combined with about 200 g (708 mmol) of coconut fatty acids. The mixture was warmed to about 60° C. and evacuated to a pressure of about 10 Ton (~1,333 N/m$^2$). A portion (about 6.1 mL or 70.8 mmol, 0.1 eq.) of concentrated (about 70%) perchloric acid was added slowly over the course of about 5 minutes and the solution was allowed to stir for about 24 hours. The reaction proceeded as shown by the reaction scheme I, above.

After 24 hours, the vacuum was broken and 2-ethyl-1-hexanol (about 110.6 g, 1.2 eq) was added. The flask was again evacuated to about 10 Torr and the reaction allowed to proceed for about 2 hours more, prior to cooling. Potassium hydroxide (about 4.77 g or 85 mmol, 0.12 eq.) dissolved in about 50 mL water was then added to quench the reaction and the layers were allowed to separate. The crude estomer was decanted from the water and distilled at a temperature within the range of between about 180° C. and about 190° C., at a pressure within the range of between about 0.1 Torr and about 0.5 Torr, to remove excess alcohol, monomer and side products such as lactones.

Example 2

Testing the Oxidation Resistance and Deposit Formation

A natural estomer was tested for resistance to high temperature oxidation and deposits formation. The natural estomer was tested against vegetable oils, PAO, and mineral oil formulations. The test was conducted as follows. The testing was performed in a custom apparatus that was designed to run eight test samples simultaneously called the Rotating thin-film and bulk thermo-oxidation test. The samples are placed in individual glass vials and loaded into a heating block. The sample size can range from 15 to 40 ml; about 20 ml was used for this testing. The heated block can be accurately controlled to 1° C., in a range of 120 to 180° C., the test was run at 160 C. The block was mounted at an angle of 35 degrees from normal and was attached to a stepper motor to allow the block to rotate. The test was conducted at atmospheric pressure conditions.

Rotation of the block with the samples at an angle simulates both bulk and thin film oxidation while also allowing for a measure of deposit formation on the walls of the sample vials. The block was rotated at a speed of 2 rpm for this testing. Samples were characterized every 24 hrs for viscosity. The test was run until all samples had a 200% increase in viscosity from the beginning of the test. The samples were removed from the block and the glass vial surface was characterized for deposit formation.

The rating of the deposits in this test is based on the amount of oil oxidation-degradation products, such as lacquer, which become deposited on the aluminum surface of the shaft. The rating is made visually by classifying the deposits as follows: 1 indicates a clean surface or extremely light deposit; 2, moderately light or iridescent surface; 3, light or golden deposit and transparent; 4, medium or brown and translucent; 5, heavy or brown and opaque; and 6, very heavy black or brown and rough.

The results are shown in Table 8. As can be seen, the ratings achieved for the compositions comprising the chemically modified algal oils (i.e., oleic estomer, with or without an antioxidant) are superior to those for natural and mineral oils.

TABLE 8

Test Results for Deposit Formation

| Composition | Concentration, mass % | Rating |
|---|---|---|
| High Oleic Canola Oil | 100 | 6.0 |
| Commercial PAO, 6 cSt | 100 | 1.0 |
| Low Cost Mineral Oil Formulation | 100 | 4.5 |
| Oleic Estomer | 100 | 2.5 |
| Oleic Estomer + Antioxidant | 100 | 1.5 |

The oxidation properties of the natural estomer base oil was tested against the PAO base oil and a couple of natural high performance vegetable oils in the rotating oxidation test. This test has been designed to simulate the thin-film and bulk oxidation conditions found in combustion engines was conducted as follows.

Initial testing was performed to characterize the performance of estomer base oil from natural sources versus a couple of the best known vegetable oil performers for oxidation stability, HO canola and HO sunflower oils. A fully synthetic petroleum based PAO6 was also included in the testing to demonstrated the performance of the estomer vs the current reference base oil for lubricant production.

Figure 3:
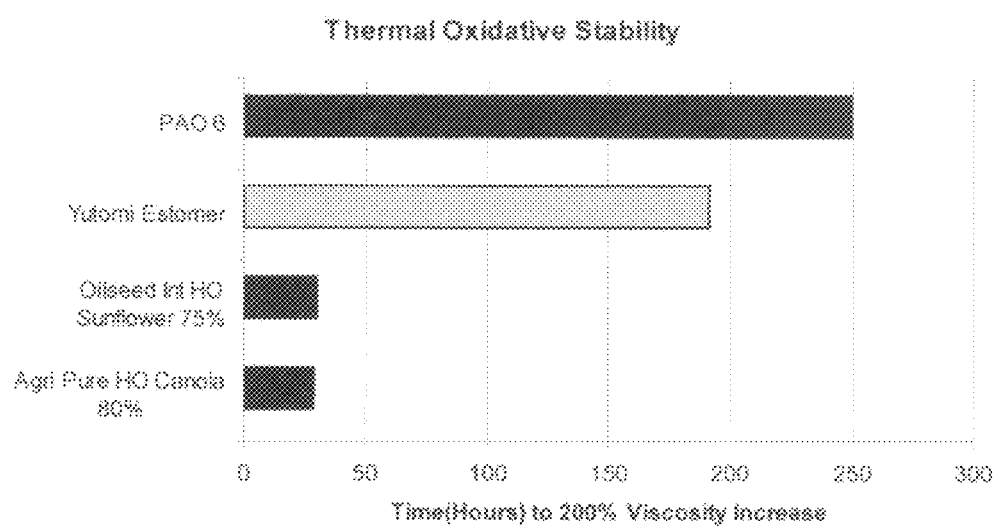
FIG. 3 illustrates schematically oxidation data on performance of some existing high performance vegetable oils, PAO, and compositions.

As can be seen, the estomer outperformed the unmodified vegetable oils by a large margin. The estomer demonstrated much closer oxidative performance characteristics to the PAO 6 reference base oil and showed a large increase in stability, as illustrated by FIG. 3, demonstrating performance that is comparable to that of a PAO.

Figure 4:
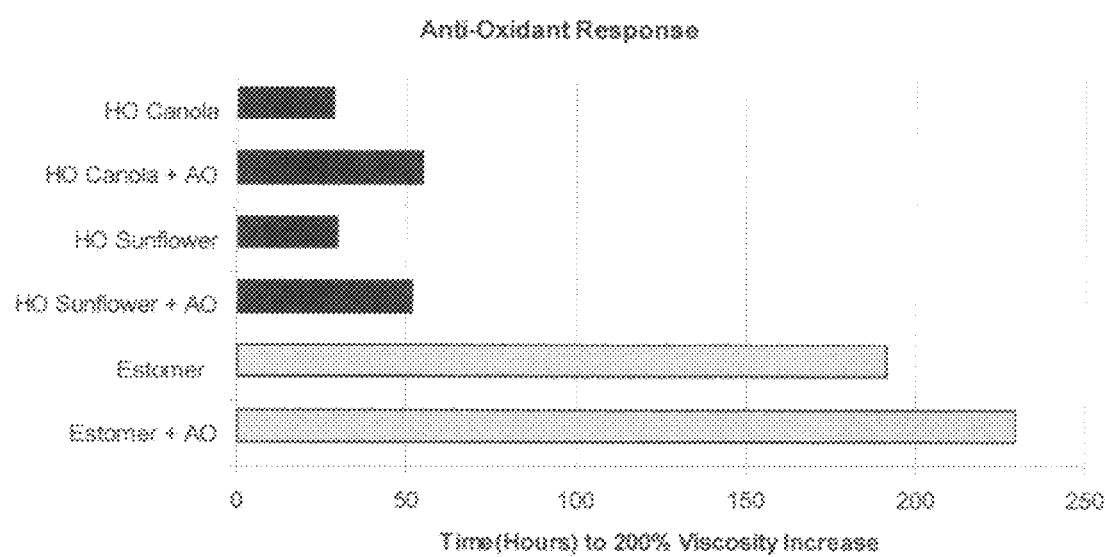
FIG. 4 illustrates schematically comparative data on the anti-oxidant response of some of our compositions and existing vegetable oils.

Additional testing was performed to develop an anti-oxidant package for the estomer base oils and create a representative formulation that could be used for many of the applications described in this patent. Additives from Lubrizol and Ciba Corporation were used in the development of the AO package. Some of the results are summarized in FIG. 4. As can be seen, the unmodified vegetable oils had excellent response to the AO package as seen with the near doubling of their life in the testing. The estomer did not show as strong of a response but the AO package boosted the performance level of the base oil to the point that is necessary for use in modern motor oil formulations.

Although our methods and systems have been described with reference to the above-discussed reactions and structures, it will be understood that modifications and variations are encompassed within the spirit and scope of the disclosure as defined in the appended claims.

What is claimed is:

1. A base stock, comprising chemically modified algal oil comprising a compound including a moiety having a chemical structure 1:

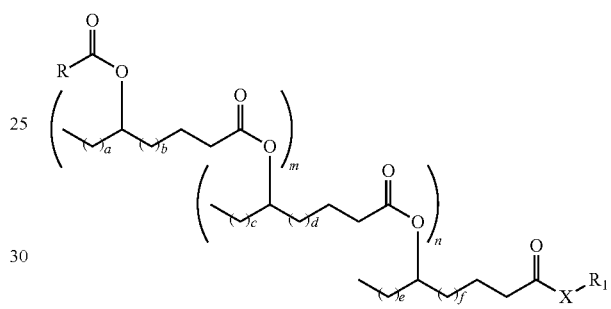

wherein:
R is a linear $C_{1-18}$ alkane;
each of m and n is selected from the group consisting of 0 and a positive integer, wherein both m and n cannot be 0;
each of the sums (a+b) and (c+d) is selected from the group consisting of 1, 3, 5, 7, 9, 11, 13, and 15;
the sum (e+f) is selected from the group consisting of 9, 11, 13, and 15;
X is selected from the group consisting of NR2, O and S; and
each of $R_1$ and $R_2$ is a $C_{1-30}$ hydrocarbon optionally containing linear, branched, saturated, unsaturated and/or aromatic functionalities.

2. The base stock of claim 1, wherein R is a linear $C_5$-$C_{13}$ alkane, comprising the aliphatic portion of a fatty acid selected from the group consisting of hexanoic acid, octanoic acid, capric acid, lauric acid, and myristic acid.

3. The base stock of claim 1, wherein the chemically modified algal oil is obtained by chemical modification of an oil extracted from at least one species of algae selected from the group consisting of *Botryococcus*, *Atractophora hypnoides* P.L.Crouan and H.M.Crouan, *Ascophyllum nodosum*, *Charales*, *Codium*, *Fucus*, *Haematococcus*, *Ulva lactuca*, *Laminaria*, *Lemanea*, *Macrocystis*, *Mastocarpus stellatus*, *Pelvetia canaliculata*, *Palmaria palmate*, *Porphyra*, *Postelsia palmaeformis*, *Scenedesmus obiquus*, *Scenedesmus qudricauda*, *Scenedesmus dimorphus*, *Chlamydomonas rheinhardii*, *Chlorella vulgaris*, *Chlorella pyrenoidosa*, *Spirogyra* sp., *Dunaliella bioculata*, *Dunaliella salina*, *Euglena gracitis*, *Prymnesium parvuum*, *Tetraselmis maculata*, *Porphyridium cruentum*, *Spirutina platensis*, *Spirutina maxima*, *Synechoccus* sp., *Anabaena cylindrica*, *Ankistrodesmus*, *Botryococcus braunii*, *Dunaliella bardawii*, *Isochrysis* sp., *Nannochloris* sp., and *Nitzschia* sp.

4. The basestock of claim 1, wherein the species of algae is *Botryococcus braunii*.

5. The basestock of claim 1, wherein the species of algae includes a genetically modified strain.

6. A lubricant base oil, comprising a chemically modified algal oil comprising a compound including a moiety having a chemical structure 1:

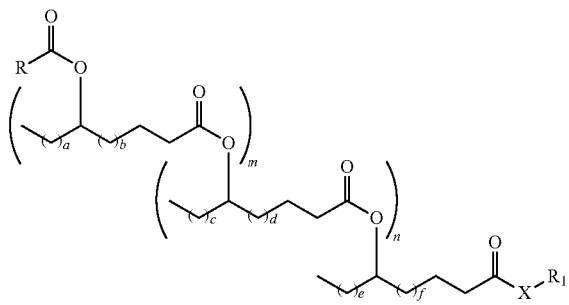

wherein:
R is a linear $C_{1-18}$ alkane;
each of m and n is selected from the group consisting of 0 and a positive integer, wherein both m and n cannot be 0;
each of the sums (a+b) and (c+d) is selected from the group consisting of 1, 3, 5, 7, 9, 11, 13, and 15;
the sum (e+f) is selected from the group consisting of 9, 11, 13, and 15;
X is selected from the group consisting of NR2, O and S; and
each of $R_1$ and $R_2$ is a $C_{1-30}$ hydrocarbon optionally containing linear, branched, saturated, unsaturated and/or aromatic functionalities.

7. The base oil of claim 6, wherein the chemically modified algal oil is obtained by chemical modification of an oil extracted from a species of algae which produces greater than 30% oleic acid.

8. The base oil of claim 6, wherein the chemically modified algal oil is obtained by chemical modification of an oil extracted from a species of algae which produces a high lipid content that is equal to or greater than 70% of the weight.

9. The base oil of claim 6, wherein the chemically modified algal oil is obtained by chemical modification of an oil extracted from a species of algae which is grown to produce a fatty acid yield greater than 80% by weight (dry).

10. The base oil of claim 6, wherein the chemically modified algal oil is obtained by chemical modification of internal olefins extracted from a species of algae.

11. A lubricant formulation that comprises chemically modified algal oil comprising a compound including a moiety having a chemical structure 1:

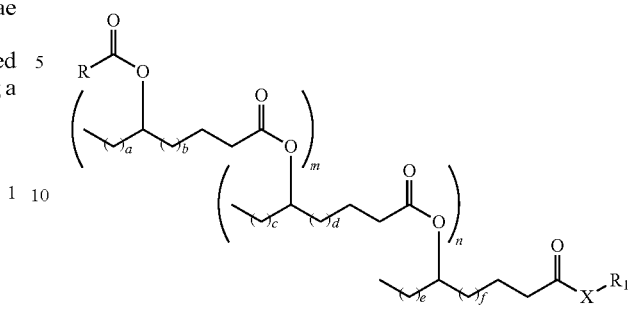

wherein:
R is a linear $C_{1-18}$ alkane;
each of m and n is selected from the group consisting of 0 and a positive integer, wherein both m and n cannot be 0;
each of the sums (a+b) and (c+d) is selected from the group consisting of 1, 3, 5, 7, 9, 11, 13, and 15;
the sum (e+f) is selected from the group consisting of 9, 11, 13, and 15;
X is selected from the group consisting of NR2, O and S; and
each of $R_1$ and $R_2$ is a $C_{1-30}$ hydrocarbon optionally containing linear, branched, saturated, unsaturated and/or aromatic functionalities.

12. A lubricant composition comprising the base oil of claim 6, and at least one additive.

13. The lubricant composition of claim 12, wherein the additive is selected from the group consisting of a detergents, an anti-wear agent, an antioxidant, a viscosity index improver, a dispersant, a pour point depressant, a corrosion protector, a friction coefficient modifier, a metal deactivator, a compatibility agent, a colorant, an extreme pressure additive, an antifoam agent, a defoamant, a demulsifier, and any combination thereof.

14. The lubricant composition of claim 12, wherein the amount of the additive is between about 5 mass % and about 20 mass %, based on the weight of the composition.

15. The lubricating composition of claim 12, wherein the composition is adapted for use in internal combustion engines.

16. A lubricant composition comprising the base oil of claim 6, and at least one additional base oil.

17. The lubricant composition of claim 16, wherein the additional base oil is selected from the group comprising Group I, II, III, IV, and V from the API base oil classification.

* * * * *